United States Patent [19]
Gawin et al.

[11] Patent Number: 5,114,942
[45] Date of Patent: May 19, 1992

[54] TREATING HABIT DISORDERS

[75] Inventors: Frank H. Gawin, New Haven, Conn.; Brian G. Humblestone; David F. Allen, both of Nassau, The Bahamas

[73] Assignee: Yale University, New Haven, Conn.

[21] Appl. No.: 641,378

[22] Filed: Jan. 15, 1991

Related U.S. Application Data

[62] Division of Ser. No. 331,923, Mar. 31, 1989, Pat. No. 5,059,600.

[51] Int. Cl.$^5$ .................. A61K 31/38; A61K 31/40; A61K 31/445; A61K 31/495
[52] U.S. Cl. .................. 514/255; 514/320; 514/427; 514/432
[58] Field of Search .............. 514/255, 320, 422, 432

[56] References Cited

U.S. PATENT DOCUMENTS

| | | |
|---|---|---|
| 2,554,736 | 5/1951 | Haefliger et al. . |
| 3,058,979 | 10/1962 | Ullyot . |
| 3,192,204 | 6/1965 | Craig et al. . |
| 3,194,733 | 7/1965 | Yale et al. . |
| 3,196,157 | 7/1965 | Janssen et al. . |
| 3,238,216 | 3/1966 | Janssen et al. . |
| 3,310,553 | 3/1967 | Bloom et al. . |
| 3,412,193 | 11/1968 | Coppola . |
| 3,438,991 | 4/1969 | Janssen et al. . |
| 3,546,226 | 12/1970 | Schmutz et al. . |
| 3,663,696 | 5/1972 | Howell et al. . |

OTHER PUBLICATIONS

Evolving Conceptualizations of Cocaine Dependence; Frank H. Gawin, the Yale Journal of Biology and Medicine Inc., pp. 123-136, 1988.
Abstinence Symptomatology and Psychiatric Diagnosis in Cocaine Abusers; F. Gawin & H. Kleber; Arch Gen Psychiatry, vol. 43, Feb. 1986, pp. 107-113.
Desipramine Facilitation of Initial Cocaine Abstinence, F. Gawin & H. Kleber; Arch Gen Psychiatry, vol. 46, Feb. 1989, pp. 117-121.
Depression-Inducing and Antidepressive Effects of Neuroleptics, Neuropsychobiology 10: pp. 131-136, Poldinger S. Sieberns (1983).
Flupenthixol Decanoate in Schizophrenia; H. R. Trueman & M. G. Valentine; Brit. F. Psychiat. (1974), 124, pp. 58-59.
Major Tranquilizers Used As Antidepressants, Mary M. Robertson & M. R. Trimble, Journal of Affective Disorders, 4 (1982) pp. 173-193; Elsevier Biomedical Press.
A Controlled Comparison of Flupenthixol and Amitriptyline in Depressed Outpatients; J. Young, British Medical Journal, 1976, pp. 1116-1118, vol. 1.
SCRIP No. 822, Aug. 22, 1983, p. 2.
Central Nervous System, p. 78.
The Merck Index, pp. 599-600.
Lundbeck Limited, pp. 684-685.
Chemindex Plug, p. 407.
Symptomatic Relief with Flupentixol (Fluanxol) of the Anxious-Algetic-Depressive Syndrome Complex in Neurotic States; V. Predescu; Acta Psychiat. Scand (1973) 49, pp. 15-27.
A Double-Blind Comparison of Flupenthixol Nortriptyline and Diazepam in Neurotic Depression; D. Johnson; Acts Psychiat Scand, (1979) 59, pp. 1-8.
Objective and Subjective Assessments of the Effects of Flupentixol and Benzodiazepines on Human Psychomotor Performance; M. Mattila Psychopharmacology (1988) 95: pp. 323-328.
Flupenthixol Versus Combined Fluphenazine-Nortriptyline in Depressive Illness; Practitioner, Mar. 1981, vol. 225, J. Conway, pp. 400-404.
Repeated Cocaine Administration Results in Supersensitivity of Straital D-2 Dopamine Autoreceptors to Pergolide, Linda Dwoskin; 1988 Pergamon Journals Ltd.; Life Sciences, vol. 42, pp. 255-262.
A Controlled Comparison of Flupenthixol Decanoate Infections and Oral Amitriptyline in Depressed Out-Patients; W. Tam Young; Brit. J. Psychiat, (1982), 140, pp. 287-291.

Primary Examiner—S. J. Friedman
Attorney, Agent, or Firm—Frishauf, Holtz, Goodman & Woodward

[57] ABSTRACT

A method for treating habit disorders in a human patient comprising administering to the patient an antihabitual amount of a pharmaceutically active compound, which results in activation of a brain reward system, e.g., flupenthixol, or esters thereof or pharmaceutically acceptable salts thereof, either alone or in admixture with a physiologically acceptable diluent.

6 Claims, 2 Drawing Sheets

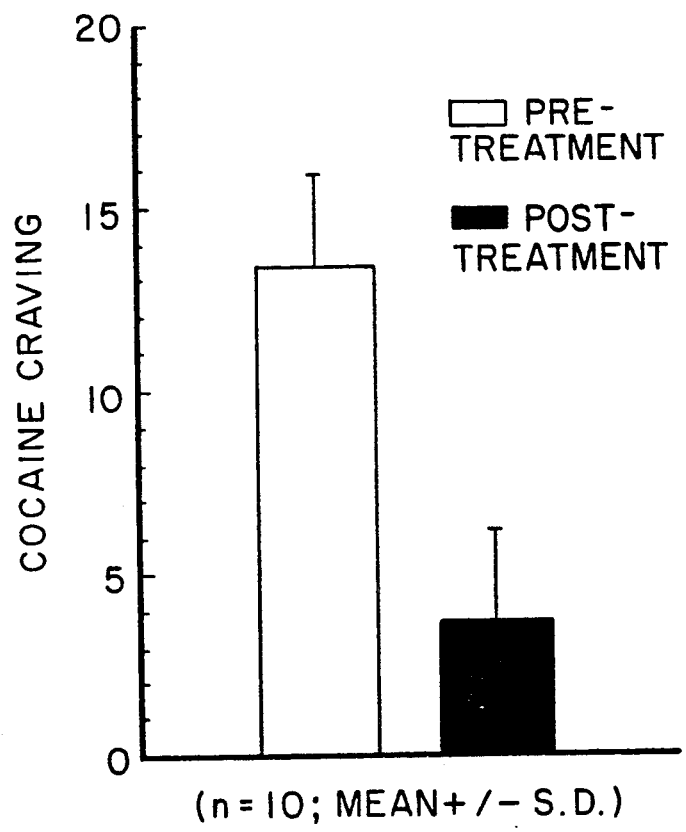

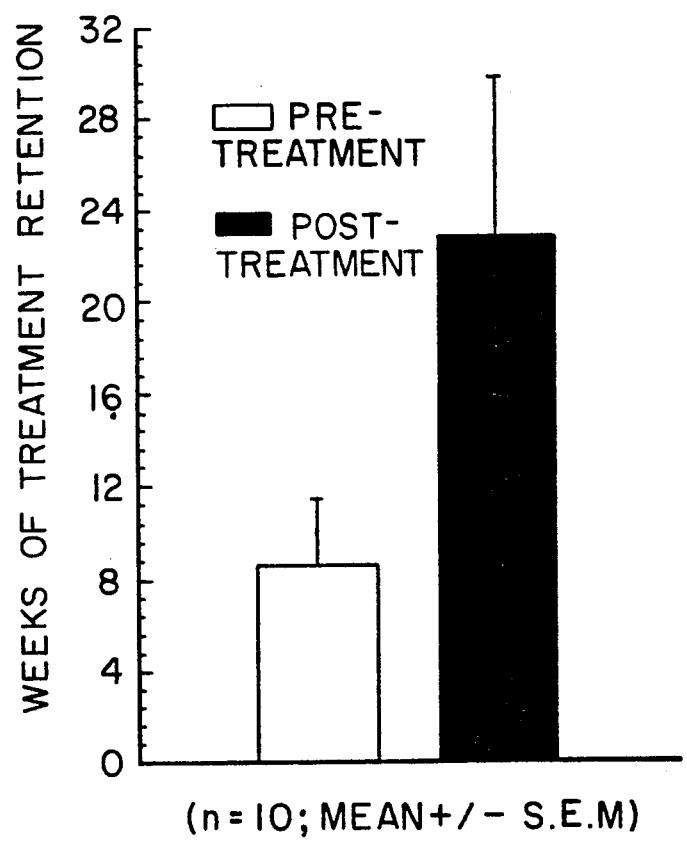

TREATING HABIT DISORDERS

GOVERNMENT RIGHTS

This invention was made with United States government support under Grant No. P50-DA04060 awarded by the Department of Health and Human Services. The United States Government has certain rights in the invention.

This is a division of application Ser. No. 331,923, filed Mar. 31, 1989, now U.S. Pat. No. 5,059,600.

BACKGROUND OF THE INVENTION

1. Field of the Invention

The present invention concerns treating patients suffering from adverse habits or cravings by administering a pharmaceutically active compound, which compound results in activation of a brain reward system.

2. Background Information

Habit disorders have a substantial consequence for health. The course of various habit disorders may be positively affected by therapeutic psychopharmacological agents that influence the nervous system. The commonality between various habit disorders is a neurophysiological state expressed by the craving or desire for the habit.

One of the most problematic and prototypal examples of a habit disorder is "crack" cocaine smoking. "Crack" cocaine smoking has now produced epidemic cocaine dependence in the urban United States, following earlier epidemic abuse in the Bahamas (Jekel, J. F., Allen, D. F., Podlewski, H., Clarke, N., Dean-Patterson, S., Cartwright, P., "Epidemic Cocaine Free-Base Abuse: Case Study from the Bahamas", *Lancet*, (1986), 1, 459-462).

Cocaine smoking and intravenous cocaine injection are equi-potent in their central effects and in their abuse liability (Gawin, F. H., Ellinwood, E. H., "Cocaine and Other Stimulants; Actions, Abuse, and Treatment", *New Engl. J. Med.*, (1988), 318, 1173-1182 and Gawin, F. H., Kleber, H. D., "Evolving Conceptualizations of Cocaine Dependence", *Yale J. Biol. Med.*, (1988), 123-136).

"Crack" is defined as cocaine distributed in ready-to-smoke form (cocaine free base), rather than as the injectable or insufflatable cocaine hydrochloride. Previously, cocaine smoking ("freebasing") required a complex extraction by the end user, of free cocaine base from cocaine hydrochloride, limiting the availability and thus the extent of cocaine dependence by smoking (Gawin and Ellinwood, supra).

"Crack" is generally sold in small, inexpensive one or two inhalation quantities, in a marketing system that, in contrast to prior cocaine distribution, saturates a region with ubiquitous "street" cocaine distributors. The combination of low initial expense, unprecedented availability, and extreme abuse liability has resulted in an epidemic of refractory, recurrent cocaine dependence, making obvious the limits of current cocaine abuse treatment strategies for "Crack" abuse, and has lead to unprecedented levels of public concern.

Cocaine withdrawal is characterized by a protracted anhedonic dysphoria (Gawin, F. H., Kleber, H. D., "Abstinence Symptomatology and Psychiatric Diagnosis in Chronic Cocaine Abusers", *Arch. Gen. Psychiatry*, (1986), 43, 107-113) that produces craving for cocaine (Jekel et al, supra). Episodically superimposed on this craving is an additional pulsatile craving produced by exposure to conditioned cues (independent stimuli present during past episodes of cocaine euphoria) (Jekel et al, supra). Such cues evoke vivid memories of extreme cocaine euphoria. The likelihood of continued cocaine smoking in an abuser is related to the strength of the craving experienced from these two sources.

In "crack" abuse, the withdrawal dysphoria is combined with ubiquitous cocaine sales and availability, and hence ubiquitous presence of conditioned cues, to produce an intractable abuse that has been considered, by many, to be impossible to treat without hospitalization, (Jekel et al, supra and Grabowski, J., Dworkin, S. I., "Cocaine: An Overview of Current Issues", *Int. J. Addict*, (1985), 20, 1065-88). Unfortunately, the crack epidemic has appeared in impoverished populations with very limited access to inpatient resources.

Prior outpatient pharmacotherapy trials for cocaine dependence demonstrate that high-dose heterocyclic antidepressants are effective in reversing cocaine withdrawal craving, but that their efficacy is delayed by 10-14 days from the onset of therapy (Giannini, A. J., Malone, D. A., Giannini, M. C., Price, W. A., Loiselle, R. H., "Treatment of Depression in Chronic Cocaine and Phencyclidine Abuse with Desipramine", *J. Clin. Pharmacol.*, (1986), 26, 211-4 and Gawin, F. H., Kleber, H. D., Byck, R., Rounsaville, B., Kosten, T. R., Jatlow, P., Morgan, C., "Desipramine Facilitation of Initial Cocaine Abstinence", *Arch. Gen. Psychiatry*, (1989) Arch. Gen. Psychiatry, 46, 117-121. In outpatient "crack" smokers, the extreme availability of the drug often results in resumption of cocaine smoking early in treatment, producing non-compliance to voluntary oral medication regimens that usually results in cessation of all forms of treatment, including psychotherapy, before the possible onset of any therapeutic medication effects (Gawin, Kleber, Byck, Rounsaville, Kosten, Jatlow and Morgan, supra). In this context, a depot preparation or more rapidly acting agent would have advantages over other methods of medication administration.

Flupenthixol decanoate is a depot xanthene derivative with unique properties, having both rapid antidepressant activity at low doses (Poldinger, W., Sieberns, S., "Depression-inducing and Antidepressive Effects of Neuroleptics: Experiences with Flupenthixol and Flupenthixol Deanoate", Neuropsychobiology, (1983), 10, 131-136 and Robertson. M. M., Trimble, M. R., (1982), "Major Tranquilizers Used as Antidepressants", *J. Affective Dis.*, 4, 173-195) and neuroleptic activity at higher doses (Trueman, H. R., Valentine, M. G., (1974), "Flupenthixol Decanoate In Schizophrenia", *Br. J. Psychiatry*, 124, 58-59).

Flupenthixol appears to act by blocking dopamine binding to a number of receptors, including D-1, D-2, and inhibitory D-2 autoreceptors.

Although classified as a neuroleptic, and not as a typical antidepressant, low dose flupenthixol has been established as being as effective as conventional heterocyclic antidepressants in over fifteen double-bind controlled trials (Valle-Jones, J. C. and Swarbrick, D. J., (1981), A Comparative Study of Once-daily Flupenthixol in the Treatment of Elderly Depressed Patients: A Multicentre Trial in General Practice, *Curr. Med. Res. Opin.*, 7, 543-549; Wheatley, D. P., (1983), "Antidepressant Effect of Flupenthixol Compared to Miaserin", *J. Int. Biomet. Inform. Data.*, 4, 5-12; Young, J. P. P., Hughes, W. C. and Lader, M. H., (1976), "A Controlled Comparison of Flupenthixol and Amitriptyline in Depressed Out-Patients", *Br. Med. J.,* 1, 1116-1118; Johnson, D. A. W., (1979), "A Double-blind Comparison of Flupenthixol, Nortriptyline and Diazepam in Neurotic Depression", *Acta. Psychiatr. Scand.,* 59, 1-8; Presdescu, V., Ciurezu, T., Timofte, G. and Roman, I., (1973), "Symptomatic Relief with Flupenthixol (Fluanxol) of the Anxious- Algetic-Depressive Syndrome Complex in Neurotic States", *Acta Psychiat. Scand.,* 49, 15-27; Frolund, F., (1974), "Treatment of Depression in General Practice. A Controlled Trial of Flupenthixol", *Curr. Med. Res. Opin.,* 2, 78-89; Ovhed, I., (1976), "A double-blind Study of Flupenthixol ('Fluanxol') in General Practice", *Curr. Med. Res. Opin.,* 4, 144; Rosenberg, I. U., Ostensen, A. I., and Fonnelop, H., "Flupenthixol- nortriptyline in the Treatment of Patients with Anxiety- Depression-Asthenia (the 'ADA syndrome')" (translation). *Tidsskr. Norske. Laegeforen.,* 96, 229-233; Sederberg-Olsen, A. P., Lauritsen, B., Husfeldt, P., Ronne, H., Ekstrome, K., Bjorndal, F., Holst, B. and Jakobsen, K., (1979), "Depressive Tilstande, Forekomst og Behandling i Almen Praksis", *Uqeskr. Laeq.,* 143, 1383-1387; Wheatley, D. P., (1983), "Antidepressant Effects of Flupenthixol Compared to Mianserin. A report from the Psychopharmacology Branch of the General Practitioner Research Group", *Int. Biomed. Inf. Data.,* 4, Suppl. 1, 5-12; Razak, J. (unpubl. report, 1983), "Flupenthixol Versus Phenelzine in the Treatment of Neurotic Depression: A Double-Blind Trial"; Conway, J. F., (1981), "Flupenthixol Versus Combined Fluphenazine-Nortriptyline in Depressive Illness", *Practitioner,* 225, 400-404; Simmelsgaard, H., Frankel, I., Gunner-Svensson, F., Poulsen, H., Blumenthal, M., Metsa-Simola, S., Grohn, P., Reinertsen, T., Schmidt, P., Brandrup, E. and Sovso, H., (1973), "Multicentre Double-Blind Clinical Trial of Flupenthixol (Fluanxol) and Flupenthixol+Medlitracen (Lu 6722) in the Treatment of Neuroses", (translation), *Nord. Psyckiat. Tidsskr.* 27, 145-154; Baldwin, R., Cranfield, R., Swarbrick, D. J., (1983), "A Double-Blind Trial Comparing Single and Divided Daily Doses of Flupenthixol in the Treatment of Mild to Moderately Severe Depression". "A Multicentre Trial in General Practice", *J. Int. Biomet. Inform. Data,* 4, 37-42; Majiid, I., Swarbrick, D. J., (1983), "A Double-Blind Comparison of a Single Daily Dose of 1 mg or 2 mg flupenthixol Dihydrochloride in the Treatment of Depression", *J. Int. Biomet Inform. Data,* 4, 13-17; Valle-Jones, J. C., Swarbrick, D. J., (1983), "A Comparative Study of Once Daily Flupenthixol and Amitriptyline in the Treatment of Elderly Depressed Patients: A Multicentre Trial in General Practice", *J. Int. Biomet. Inform. Data,* 4, 29-35 and Tam, W., Young, J. P. R., John, G. and Lader, M. H., (1982), "A Controlled Comparison of Flupenthixol Decanoate Injections and Oral Amitriptyline in Depressed Out-Patients", *Br. J. Psychiatry,* 140, 287-291). Thus, similar to antidepressants, flupenthixol might positively influence the outcome of the treatment of the habit disorder.

Both habit forming activities (e.g., feeding) and ingestion of abused substances increase neural activity in regions of the brain that produce rewarding feelings. Different habit disorders or "addictions" have been hypothesized to be similar in that a final common pathway for their compelling properties is activation of reward systems (Wise, R. A. and Bozarth, M. A., "A Psychometer Stimulant Theory of Addiction", *Psychological Review,* 94. 469-472, (1987); Wise, R., "Neural Mechanisms of the Reinforcing Action of Cocaine", (1984), *NIDA Res. Mon. Series,* Vol. 50, U.S. Government Printing Office, Washington, D.C., pp. 15-53).

It has also been hypothesized that many chronic habit disorders (e.g., stimulant abuse and other abuses) produce compensatory adaptations in brain reward systems that produces decreased reward activity, and thus craving and other symptoms that emerge in the absence of the habitual activity. It is hypothesized that this craving is induced by decreases in dopaminergic activity, mediated by supersensitivity of inhibitory dopaminergic auto-receptors, (Gawin and Ellinwood, *New Eng. J. Med.,* (1988), 318, 1173-1182). Auto-receptor supersensitity has recently been demonstrated experimentally in animals exposed to chronic cocaine (Dwoskin, L. P., Peris, J., Yasuda, R. P., Philpott, K., Zahniser, N. R., "Repeated Cocaine Administration Results in Supersensitivity of Striatal D-2 Dopamine Autoreceptors to Pergolide", *Life Sci.,* (1988), 42, 255-262). Similar changes may mediate cravings for other habits.

Without wishing to be bound by any particular theory of operability it is believed that a low concentration of flupenthixol may demonstrate greater affinity for dopamine auto-receptors than post-synaptic receptors, and preferentially bind to these inhibitory sites, suggesting that increased dopaminergic activity, and anti-anhedonic, anti-depressant activity would follow application of low flupenthixol doses, decreasing craving for a habit. At higher dosages and plasma concentrations, as effects on post-synaptic D-1 and D-2 receptors predominate, cocaine blocking and anhedonia inducing activity might occur.

Clinically acceptable concentrations of conventional phenothiazine or butyrophenone neuroleptics may exacerbate anhedonic stimulant withdrawal symptoms (Wise et al, supra and Gawin, F. H., "Neuroleptic Reduction of Cocaine Induced Paranoia but Not Euphoria", *Psychopharmacology,* (1986), 90, 142-143) in cocaine abusers resulting in an extreme patient resistance to neuroleptic treatment.

Significantly, low dose flupenthixol has been demonstrated to lack the anhedonia-inducing effects of similar agents in animal models (Ettenburg, A., Koob, G. F., Bloom, F., "Response Artifact in Measurement of Neuroleptic-induced Anhedonia", *Science,* (1981), 213, 237-239), and to lack characteristic neuroleptic-like behavioral effect in humans (Mattila, M. J., Mattila, M., Aranko, K., "Objective and Subjective Assessments of the Effects of Flupenthixol and Benzodiazepines on Human Psychomotor Performance", *Psychchopharmacology,* (1988), 95, 323-328).

SUMMARY OF THE INVENTION

It is an object of the invention to reduce or eliminate habit disorders in humans. This object is achieved by the present invention which provides a method for treating habit disorders in humans comprising administering to a human patient suffering from a habit disorder an effective anti-habitual amount of a pharmaceutically active compound or esters thereof or pharmaceutically acceptable salts thereof, either alone, or in admixture with a physiologically acceptable diluent. Compounds for use in the present invention result in activation of brain reward systems. Non-limiting examples of pharmaceutically active compounds for use in the present invention include the following:

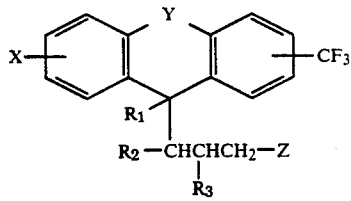 (1)

, wherein X is a halogen, SO$_2$N(CH$_3$)$_2$ or CF$_3$, Y is a member selected from the group consisting of sulfur and oxygen; R$_1$ and R$_2$ are members selected from the group consisting of hydrogen and hydroxy and, when taken together, a single bond; R$_3$ is a member selected from the group consisting of hydrogen and methyl; and Z is a member selected from the group consisting of di-lower alkylamino, di-lower alkylamino wherein one or both alkyl groups are substituted with hydroxy, N-pyrrolidinyl, N-piperidyl, and N'-lower-alkyl-N-piperazinyl, wherein the alkyl can be substituted with OH;

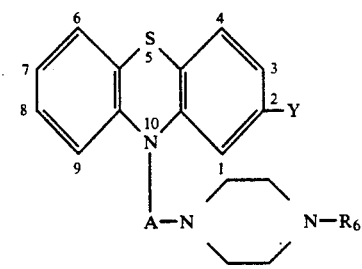

in which Y is perfluoroalkyl of 1 to 3 carbon atoms; A is an alkylene chain of from 2 to 6 carbon atoms separating the nitrogen atoms linked thereto by at least two carbon atoms, and R$_6$ is a member selected from the group consisting of cycloalkyl-lower-alkyl, the cycloalkyl portion having 5 to 6 carbon atoms and the lower -alkyl portion having 1 to 4 carbon atoms, lower alkenyl having 3 to 6 carbon atoms, hydroxy-lower-alkyl having 2 to 6 carbon atoms in the alkyl portion, hydroxy-lower alkyloxy-lower-alkyl, the lower alkyl portions having 2 to 6 carbon atoms in the alkyl portion, lower-alkanoyl having 1 to 6 carbon atoms, cycloalkyl-lower-alkanoyl, the cycle alkyl portion having 5 to 6 carbon atoms and the lower alkanoyl portion having 2 to 4 carbon atoms, phenyl-lower-alkanoyl, the lower alkanoyl portion having 2 to 4 carbon atoms, benzoyl, carbomethoxy, carbethoxy, carbonbenzoxy, carbamyl, dialkyl-carbamyl having 1 to 6 carbon atoms in the alkyl portions, N-phenyl-carbamyl, lower alkanoyloxy-lower-alkyl, the lower-alkanoyloxy portion having 2 to 6 carbon atoms and the lower-alkyl portion having 2 to 6 carbon atoms and benzoyloxy-lower-alkyl having 2 to 6 carbon atoms in the lower alkyl portion;

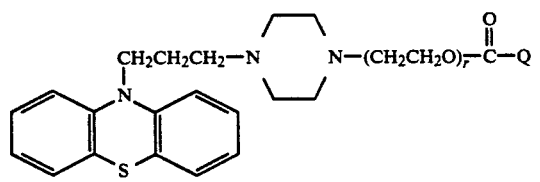

, wherein r is a positive integer from one to 2, X is chloro or triflourmethyl, Q is a higher alkyl of 6 to 14 carbon atoms, a higher alkenyl of 6 to 14 carbon atoms, a higher alkynyl of 6 to 14 carbon atoms, tolyl, dimethylbenzyl, anisyl or

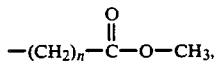

wherein n is a positive integer from 7 to 1,

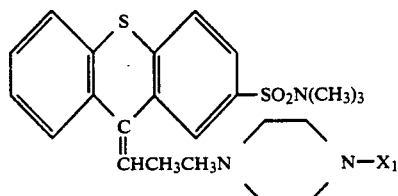

wherein X$_1$ is selected from the group consisting of methyl, 2-hydroxyethyl, 3-hydroxypropyl, dimethylsulfonamido and methylsulfonyl;

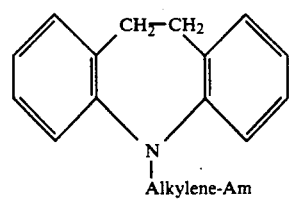

wherein alkylene represents an alkylene chain of 2-3 carbon atoms and Am represents a member selected from the group consisting of a lower molecular alkylamino radical, a low molecular dialkylamino radical, the N-piperidino-N-morpholino-, and N-pyrrolidino radicals;

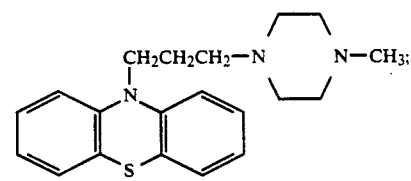

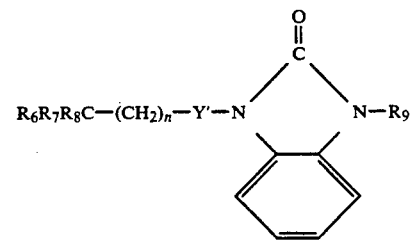

, wherein n is an integer from 2 to 5, R$_6$ is selected from the group consisting of hydrogen, hydroxy, cyano, carbamoyl and lower-alkyl-carbonyl, R$_7$ is aryl, R$_8$ is selected from the group consisting of aryl and arylmethylene, R$_9$ is selected from the group consisting of hydrogen, lower alkyl, lower-alkyl-carbonyl, lower-alkoxy-lower-alkyl, hydroxy-lower-alkyl, lower-alkoxy-carbonyl-lower alkyl, lower-alkyl-carbonyllower-alkyl, amino-lower-alkyl and halo-lower-alkyl, and Y' is selected from the group consisting of

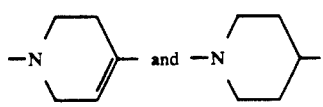

the nitrogen atom of which is attached to the

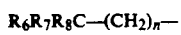

moiety; the lower alkyl and lower alkoxy having from 1 to 5 carbon atoms and the aryl being a member of the group consisting of phenyl, halophenyl, lower alkylphenyl, lower alkoxyphenyl, trifluoromethylphenyl and thienyl;

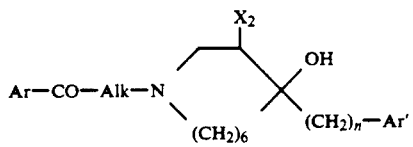

wherein Ar is a member selected from the group consisting of halophenyl, tolyl, methoxyphenyl, dimethoxyphenyl, trimethoxyphenyl, ethoxyphenyl, xylyl and (lower) alkyl-phenyl, Ar' is a member selected from the group consisting of phenyl, halophenyl, methoxyphenyl, dimethoxyphenyl, trifluoro-methylphenyl and (lower) alkylphenyl, Alk is trimethylene, $X_2$ is hydrogen or methyl and n is a positive integer smaller than three and m is zero, one or two, (9) (A) a 1,1-basic substituted dibenzoxazepine having the formula A:

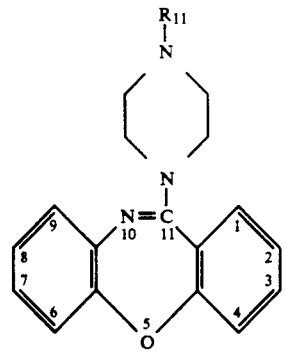

wherein $R_{11}$ is a member selected from the group consisting of hydrogen, lower alkyl, lower hydroxylalkyl, acetylated lower hydroxyalkyl, and alkoxyalkyl having not more than 5 carbon atoms, and (B) derivatives of A substituted in the benzene nuclei by at least one member selected from the group consisting of halogen, trifluoromethyl, lower alkyl, lower alkoxy, and lower alkylthio, and (C) 1,1-basic substituted dibenzoxazepines having the formula C:

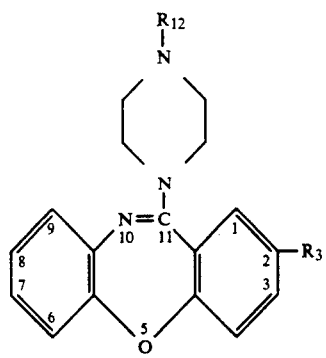

wherein $R_{12}$ represents a member selected from the group consisting of hydrogen, allyl, alkyl containing not more than 3 carbon atoms, hydroxyalkyl containing not more than 3 carbon atoms, alkoxyalkyl containing not more than 6 carbon atoms and alkoyloxyalkyl containing not more than 6 carbon atoms, $R_{13}$ is a member selected from the group consisting of nitro, amino, aminosulphonyl of the formula $SO_2NR_{14}R_{15}$ wherein $R_{14}$ and $R_{15}$ are the same or different members of the group consisting of hydrogen and methyl, alkyl-sulphinyl of the formula $-SOR_{16}$ wherein $R_{16}$ is alkyl with not more than 3 carbon atoms, and alkylsulphonyl of the formula $-SO_2R_{17}$, wherein $R_{17}$ is alkyl with not more than 3 carbon atoms;

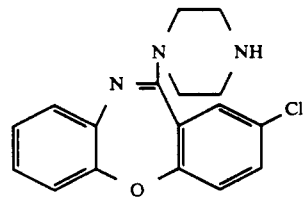

and

(11) 1—$R_{18}$—2—$R_{19}$—3—$R_{20}$—4—oxo—8—$R_2$-1—1,3,8-triaza-spiro (4,5)decane, wherein $R_{18}$ is phenyl, lower alkaryl, lower alkyl, lower alkoxyphenyl, cyclobutyl, cyclopentyl, cyclohexyl or halophenyl, $R_{19}$ is hydrogen or lower alkyl; $R_{20}$ is hydrogen, hydroxymethyl, lower alkyl, lower-alkylcarbonyl, cyano-ethyl, lower alkoxymethyl, lower alkoxycarbonyl-lower alkyl, carbamoyl-lower alkyl, cyclopropylcarbonyl, benzyl or benzoyl; $R_{21}$ is (R''')(R'''')CH — or Z'''(CH$_2$)$_p$—, wherein R''' is methyl or ethyl, R'''' is aryl, arylmethylene or arylethylene, p is a positive integer from 1 to 5 and Z''' is hydrogen, lower alkyl, hydroxy, hydroxy-lower alkoxy, phenyl, diphenyl-cyano-methylene, diaryl-hydroxymethylene, diphenylpropionyl-methylene fluorophenyl-methylene fluorophenyl-hydroxymethylene, aryloxy, 1,4-benzodioxanyl, halo-1,4-benzodioxanyl, thienyl, halophenyl, lower alkylphenyl, pyridyl, di-lower alkylphenyl,phenyl-lower alkylene, lower alkoxyphenyl, cyclopropylethylenyl, benzoyl, halobenzoyl, thienoyl, lower alkylbenzoyl, lower alkoxybenzoyl, benzoyloxy, benzyloxy, phenylmethoxymethylene, phenylhydroxymethylene, fluorophenyl-lower alkylcarbonyl-oxy-methylene, fluorophenyl-lower alkylene, aryl-lower alkyl aryl-cyclopropyl, arylthio or (aryl)(R$^{10}$)CH—, wherein R$^{10}$ is lower alkyl, aryl and aryl-lower alkyl, (aryl)$_2$CH—O—, (lower alkyl)$_2$C═CH— or (aryl)(R$^{12}$)C═CH—, wherein R$^{12}$ is hydrogen, lower alkyl, aryl or aryl-lower alkyl, the lower alkyl and lower alkoxy containing from 1 to 6 carbon atoms and the aryl being phenyl, halophenyl, lower alkylphenyl, lower alkoxyphenyl, trifluoromethylphenyl or 2-thienyl.

BRIEF DESCRIPTION OF THE DRAWINGS

FIG. 1 is a bar graph depicting cocaine craving for pre- and post-flupenthixol decanoate treatment.

FIG. 2 is a bar graph depicting weeks of treatment retention for pre- and post-flupenthixol decanoate treatment.

DETAILED DESCRIPTION OF THE INVENTION

Preferred compounds for use in the present invention include the following:

| Compound | Formula | Patent Reference |
|---|---|---|
| flupenthixol | | U.S. Pat. No. 3,192,204 |
| thiothixene ("NAVANE") | | U.S. Pat. No. 3,310,553 |
| desipramine | | Belgian Patent 614616 and British Patent 908788 |
| imipramine | | U.S. Pat. No. 2,554,736 |
| fluphenazine | | U.K. Patent 829,246<br>U.K. Patent 833,473<br>U.S. Pat. No. 3,194,733<br>U.S. Pat. No. 3,058,979 |
| perazine | | U.K. Patent 780,193 |

-continued

| Compound | Formula | Patent Reference |
|---|---|---|
| pimozide | 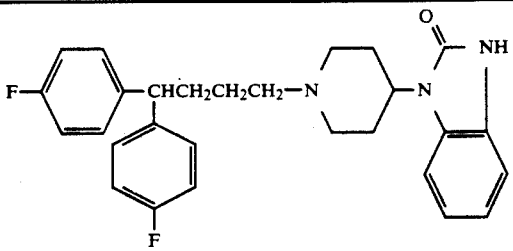 | French M3695<br>U.S. Pat. No. 3,196,157 |
| fluspirilene | 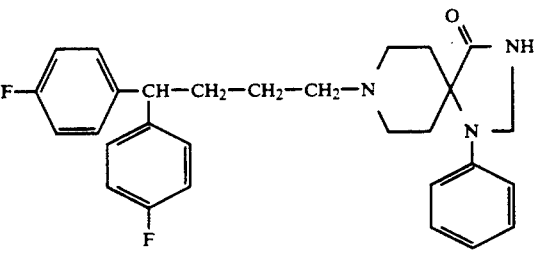 | U.S. Pat. No. 3,238,216 |
| haloperidol | 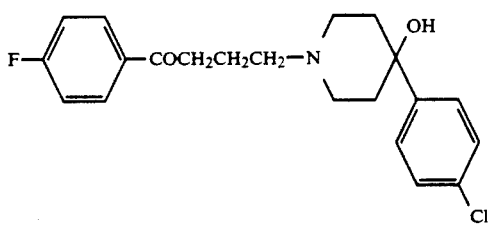 | U.S. Pat. No. 3,438,991 |
| loxapine | 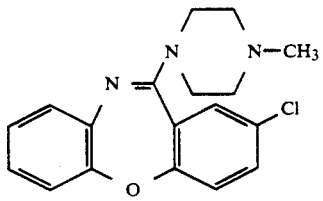 | U.S. Pat. No. 3,546,226<br>U.S. Pat. No. 3,412,193 |
| amoxapine | 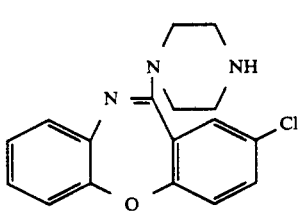 | U.S. Pat. No. 3,663,696 |
| pifluthixol (= 6-fluoro-flupenthixol) | | |

Also useful in the method of the present invention are the pharmaceutically active compounds disclosed and/or claimed, as well as pharmaceutically acceptable salts thereof and if applicable, pharmaceutically acceptable esters thereof, in the patent references listed hereinabove, the entire contents of such patent references are hereby incorporated by reference herein.

The pharmaceutically active compounds of the present invention can exist as optical isomers and both racemic and diastereomeric mixtures of these isomers which may exist for certain compounds, as well as the individual optical isomers are all within the scope of the present invention. While the racemic mixtures can be separated into their individual isomers through well-known techniques such as, for example, the separation of diastereomeric salts formed with optically active adjuncts, e.g., acids or bases followed by conversion back to the optically active substrates; in most instances, for the compounds of the present invention, the preferred optical isomer can be synthesized by means of stereospecific reactions, beginning with the appropriate stereoisomer of the desired starting material.

As indicated above, the present invention also pertains to pharmaceutically acceptable non-toxic salts of these compounds, containing, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions. Metal salts can be prepared by reacting the metal hydroxide with a compound of this invention. Examples of metal salts which can be prepared in this way are salts containing $Li^+$, $Na^+$, $K^+$. A less soluble metal salt can be precipitated from the solution of a more soluble salt by addition of the suitable metal compound. In addition, salts may be formed from acid addition of certain organic and inorganic acids, e.g., HCl, HBr, $H_2SO_4$ or organic sulfonic acids. Finally, it is to be understood that the pharmaceutically active compounds for use in the present invention in their un-ionized, as well as zwitterionic form, and/or in the form of solvates are also considered part of the present invention.

Pharmaceutically acceptable esters of compounds for use in the invention containing OH groups can also be utilized in this invention. Such esters can be prepared by esterification of the OH groups with, for example, carboxylic acids, sulphonic acids or phosphonic acid. Carboxylic acid esters derived from $C_1$-$C_{10}$-alkylcarboxylic acids, unsubstituted or substituted benzoic acids or $C_1$-$C_6$-alkyl sulphonic are non-limiting examples of acids which can be employed to produce esters for use in this invention.

The present invention can be employed to treat humans suffering from habit disorders, including substance addiction or abuse. Non-limiting examples of habit disorders which can be treated by the present invention include the following:

(1) cocaine addiction, abuse or dependency, including addiction to crack (cocaine in ready-to-smoke form), injectable cocaine and cocaine taken by nasal inhalation, (2) marijuana (THC) addiction, abuse or dependency, (3) tobacco (nicotine) addiction, abuse or dependency, (4) alcohol addiction, abuse or dependency, (5) addiction to, abuse of or dependency on halucinogens, e.g., mescaline, LSD and psylocibin, (6) addiction to, abuse of or dependency on amphetamines and other stimulants, e.g., methamphetamine and methylphenidate, (7) addiction to, abuse of or dependency on opiates, e.g., heroin, morphine, "DEMEROL" (meperidine), methadone, codeine, opium, dilaudid and fenatanyl, (8) Sedative, e.g., seconal and valium, addiction, abuse or dependency, (9) addiction to, abuse or dependency on PCP (phencyclidine, "angel dust"),

(10) addiction to, abuse of or dependency on stimulant-halucinogens, e.g., MDA, MDMA, TMA and others,

(11) eating disorders, e.g., obesity, anorexia nervosa, overeating and bulimia, and

(12) gambling disorders.

Certain components of the pharmacology of the pharmaceutically active compounds described for use in this invention, e.g., flupenthixol, particularly their interaction with monoaminergic pathways in discrete brain areas, provide a rationale for the role of the active compound, e.g., flupenthixol, in antagonizing substance addiction in general. Continued over-indulgence or inappropriate consumption of foods, as well as habitual use of other addictive substances, relies in part on "craving". In subjects suffering from substance addictions, "craving" is more of a subjective demand, for the addictive substance. The interactions of the active compound, e.g., flupenthixol with monoaminergic transmission in brain regions associated with pleasure, reward and appetite appears to result in reducing craving.

It is preferred that the pharmaceutically active compound for use in the present invention be formulated into pharmaceutical preparations. Such preparations are composed of one or more of the compounds for use in the present invention in association with a pharmaceutically acceptable carrier. The reference *Remington's Pharmaceutical Sciences,* 17th Edition, A. R. Gennaro, editor (Mack Publishing Company, 1985), discloses typical carriers and methods of preparation.

The pharmaceutically active compound described for use in the present invention can be administered topically or systemically to humans. By systemic administration is intended, oral, rectal, buccal; nasal and parenteral (i.e., intramuscular, intravenous and subcutaneous) routes. Generally it will be found that when the pharmaceutically active compound is administered orally, a larger quantity of the pharmaceutically active compound is required to produce the same effect as the smaller quantity given parenterally. In accordance with good clinical practice, it is preferred to administer the pharmaceutically active compound at a concentration level that will produce effective antihabitual effects without causing any harmful or untoward side effects and without resulting in a neuroleptic effect in the patient.

Therapeutically, the pharmaceutically active compound is preferably administered as a pharmaceutical composition comprised of an effective anti-habitual amount of the pharmaceutically active compound or a pharmaceutically acceptable salt thereof or an ester thereof and a pharmaceutically acceptable carrier, as stated herein. Pharmaceutical compositions for effecting such treatment will contain a major or minor amount, e.g., from 95 to 0.5% of the pharmaceutically active compound in combination with a pharmaceutical carrier, the carrier comprising one or more solid, semi-solid, or liquid diluents, fillers and formulation adjuvants which are non-toxic inert and pharmaceutically acceptable. Such pharmaceutical compositions are preferable in dosage unit form, i.e., physically discrete units containing a predetermined amount of the drug corresponding to a fraction or multiple of the dose which is calculated to produce the desired therapeutic response. Other therapeutic agents can also be present.

Pharmaceutical compositions providing from about 1 to 50 mg of the pharmaceutically active compound per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents, (e.g., syrup, acacia, gelatin, sorbitol, tragacanth or polyvinylpyrrolidone), fillers (e.g., lactose, sugar, corn starch, calcium phosphate, sorbitol or glycine), lubricants (e.g., magnesium stearate, talc, polyethylene glycol or silica), disintegrants (e.g., starch) and wetting agents (e.g., sodium lauryl sulfate). Solutions or suspensions of the pharmaceutically active compound with conventional pharmaceutical vehicles are employed for parenteral compositions, such as an aqueous solution for intravenous injection or an oily suspension for intramuscular injection. Such compositions having the desired clarity, stability and adaptability for parenteral use are obtained by dissolving from 0.1% to 10% by weight of the pharmaceutically active compound in water or a vehicle comprising a polyhydric aliphatic alcohol, such as glycerine, propylene glycol and polyethylene glycol or mixtures thereof. The polyethylene glycols comprise a mixture of non-volatile, usually liquid, polyethylene glycols which are soluble in both water and organic liquids and have molecular weights from about 200 to 1500.

On the basis of testing, an intramuscular effective dose of the pharmaceutically active compound, e.g., flupenthixol, could be expected to be from about 2 to about 80 mg weight with about 2 to 60 mg a preferred dosage range and preferably 2 to 20 mg. For pifluthixol an intramuscular effective dose could be expected to be 1 to 20 mg, preferably 1 to 10 mg. Such dose to be administered every 10 to 20 days. For clinical applications, however, the dosage and dosage regimen in each case should be carefully adjusted, utilizing sound professional judgment and consideration of the age, weight and condition of the recipient, the route of administration and the nature and gravity of the habit or craving. The dosage may vary based on the medical status of the recipient, e.g., dosages may have to be decreased in cases of impaired metabolism or increased in cases of enhanced metabolism. In some instances, a sufficient therapeutic effect can be obtained at lower doses, while in others, larger doses will be required.

The specific habit or craving sought to be controlled by this invention may influence the mode and frequency of administration. For example, for crack addiction, intramuscular administration is preferred, however, for tobacco addiction, a slow release administration, e.g., transdermal patches or slow dissolving tablets or capsules, may be preferred.

The invention will now be described with reference to the following non-limiting examples.

EXAMPLES

Subjects

Ten outpatients at a drug abuse treatment program were selected as subjects. All subjects smoked cocaine and met the study criteria of over 50 grams of cocaine use during the preceding 12 weeks. All subjects also met inclusion criteria of having failed to attain abstinence during treatment exposure of at least three weeks within the preceding 12 months. All subjects also met DSM-IIIR (Diagnostic and Statistical Manual of the American Psychiatric Association, Third Edition, revised) criteria for cocaine dependence. Subjects who met DSM-IIIR criteria for current or past abuse or dependence on another substance of abuse, or for major psychiatric disorder, were excluded. Subjects were also excluded if major axis I psychiatric disorder other than substance abuse occurred in a first degree relative, based on proband interview. Major medical illness was ruled out for all subjects by medical history interviews and physical examinations.

Assessments

The subjects were evaluated in at least weekly clinical contacts. Patients were given semi-structured interviews based on an abbreviated version of the weekly cocaine use inventory and craving scale. Subjects also submitted at least weekly urine specimens for analysis of cocaine metabolites and other drug use. Reports were also solicited from drug-free significant others on a biweekly basis to substantiate subject reports.

Procedure

Subjects were assessed for current or past major psychiatric disorder using DSM-IIIR criteria in a 45 minute intake interview. The subjects had all used cocaine within one week of beginning the trial. They were provided with an initial dose of intramuscular benztropine (4mg) for prophylaxis against possible extrapyramidal reactions (no subject demonstrated such a reaction or required a second benztropine dose). Subjects were then given 20 mg (N=8) or 10 mg (N=2) intramuscular (IM) flupenthixol decanoate.

All subjects were admitted to an outpatient drug treatment program, and all were provided psychotherapeutic treatment-as-usual, including daily group meetings and weekly individual psychotherapy contacts.

Urine specimens from the subjects were analyzed for benzoylecgonine using enzyme immuno-assay techniques.

Results

Nine of the ten subjects reported substantial amelioration of cocaine craving within three days of flupenthixol administration. Flupenthixol decanoate was well-tolerated in these subjects. Neither extrapyramidal effects or exacerbation of anhedonia were described. Craving for cocaine decreased by 72% (means $+/-$SEM; $13.4+/-0.8$ v $3.7+/-0.8$, $t=9.80$ (paired), $p=0.001$) at the end of the first week of treatment (FIG. 1) and remained decreased. Individual subject characteristics and response characteristics are described in Table 1.

TABLE 1

SUBJECT CHARACTERISTICS AND RESPONSE CHARACTERISTICS

| Age | Sex | Cocaine Use/Week | Other Drugs Used | Prior Treatment | Response to Flupenthixol |
|---|---|---|---|---|---|
| 30 | female | 6 gms | MJ ETOH | Three attempts up to one month duration continuous use. | Decreased depression at decreased craving at three days cocaine use in first week, then abstinence through 62 weeks. |
| 37 | male | 13 gms | MJ | Five months in treatment with continuous use. | Decreased depression at day two decreased craving at day two abstinent through 5 months of flupenthixol treatment. |
| 34 | female | 8 gms | MJ | Four early terminations without engagement in treatment. | Abstinent 10 weeks, sporadic use for 6 weeks, abstinent for 9 months; Flupenthixol discontinued at 22 weeks. |
| 35 | male | 18 gms | ETOH | Seven months in treatment with continuous use. | Sixteen weeks of abstinence on Cis-Flupenthixol followed by 6 weeks of sporadic use; abstinent for 8 following months. |
| 33 | male | 33 gms | ETOH | Four months in treatment with intermittent use. | Use in first week; abstinent through 13 weeks of flupenthixol treatment. |
| 25 | male | 8 gms | MJ | Six weeks in treatment with weekly use then full relapse. | Use in first week, abstinent through 12 weeks of flupenthixol treatment. |
| 22 | male | 23 gms | MJ | Three weeks in treatment with intermittent use. | Abstinent through 12 weeks of flupenthixol treatment; craving decrease at day 2. |

TABLE 1-continued

SUBJECT CHARACTERISTICS AND RESPONSE CHARACTERISTICS

| Age | Sex | Cocaine Use/ Week | Other Drugs Used | Prior Treatment | Response to Flupenthixol |
|---|---|---|---|---|---|
| 30 | male | 2 gms | MJ ETOH | Three weeks in treatment with intermittent use. | Use in first week abstinent through 12 weeks of flupenthixol treatment. |
| 25 | female | 14 gms | MJ ETOH | Three weeks in treatment with continuous use. | Craving decrease at day 2 abstinent through 10 weeks of flupenthixol treatment. |
| 25 | male | 4 gms | MJ | Three weeks in treatment with continuous use. | Dropped out immediately after flupenthixol. Returned to treatment 2 months later. |

MJ = marijuana
ETOH = ethanol

Eighty-eight per cent of the subjects ceased all cocaine use during the first treatment week, and the remainder in the second week, of flupenthixol decanoate treatment. Responding subjects uniformly described an amelioration of dysphoric symptoms, including anhedonia. Seventy-seven per cent of the subjects described a clear increase in energy by the third day after injection. Seventy-seven per cent of the subjects also reported substantial decreases in the magnitude of craving induced by environmental cues. Contrasted to prior maximum stays in treatment, the duration of retention in treatment was increased 260% (means $+/-$SEM; $8.7+/-2.7$ v $23.0+/-6.9$, $t=2.61$ (paired), $p=0.028$)

Compared to prior medication regimens employed with these subjects (using heterocyclic antidepressants) both compliance to psychotherapeutic treatment and retention were markedly improved.

The one non-responding subject dropped out almost immediately after 10 mg flupenthixol administration. He was subsequently readmitted after a full relapse lasting over 2 months. Both he, and other subjects treated informally before this study at higher doses, described more neuroleptic-like effects than the responding subjects, including anhedonia, increased rather than decreased craving for cocaine, and often diminished intensity or duration of cocaine's euphoric effects, but not complete blockade, when cocaine smoking was resumed. These flupenthixol effects directly produced substantial subjective distress, refusal of further flupenthixol administration (rather than subject use of the blocking effects to aid treatment) and discontinuation of treatment.

Discussion of Results

Flupenthixol decanoate effectively reduced craving for cocaine and facilitated abstinence in this sample. This is believed to be the first report of practical clinical efficacy for a depot preparation in stimulant abusers, and the first report of pharmacological efficacy for a treatment specific for "crack" abuse.

Flupenthixol decanoate was well tolerated, markedly and rapidly decreased cocaine craving and use, and produced a 260 per cent increase over prior treatments in average time retained in treatment.

It will be appreciated that the instant specification is set forth by way of illustration and not limitation, and that various modifications and changes may be made without departing from the spirit and scope of the present invention.

What is claimed is:

1. A method for treating drug disorders in a human comprising administering to said human an effective anti-habitual amount of a pharmaceutically active compound or an ester thereof or a pharmaceutically acceptable salt thereof, either alone, or in admixture with a physiologically acceptable diluent, said pharmaceutically active compound resulting in activation of brain reward systems, wherein th compound is of the formula

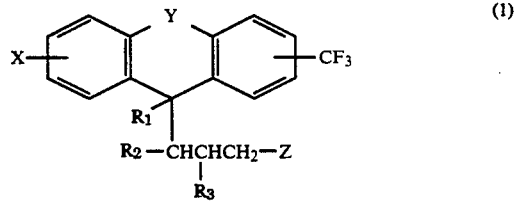

(1)

, wherein X is a halogen, $SO_2N(CH_3)_2$ or $CF_3$; Y is sulfur; $R_1$ and $R_2$ are members selected from the group consisting of hydrogen and hydroxy and, when taken together, a single bond; $R_3$ is a member selected from the group consisting of hydrogen and methyl; and Z is a member selected from the group consisting of unsubstituted di-lower alkylamino and di-lower alkylamino wherein one or both alkyl groups are substituted with a substituent selected from the group consisting of hydroxy, N-pyrrolidinyl, N-piperidyl and N'-lower-alkyl-N-piperazinyl, wherein the alkyl is unsubstituted or substituted with OH, except for treating drug disorders by administering flupenthixol.

2. A method according to claim 1, wherein the compound is administered intramuscularly.

3. A method according to claim 1, wherein said amount is 2 to 60 mg administered once every 10 to 20 days.

4. A method according to claim 1, wherein said amount is 2 to 20 mg administered once every 10 to 20 days.

5. A method according to claim 1, wherein the drug disorder is crack addiction, abuse or dependency.

6. A method according to claim 1, wherein the drug disorder is cocaine addiction, abuse or dependency.

* * * * *

UNITED STATES PATENT AND TRADEMARK OFFICE
CERTIFICATE OF CORRECTION

PATENT NO. : 5,114,942

DATED : May 19, 1992

INVENTOR(S) : GAWIN, et al

It is certified that error appears in the above-identified patent and that said Letters Patent is hereby corrected as shown below:

Column 2, line 53:

After "Flupenthixol", insert --, also called flupentixol,--

Signed and Sealed this

Second Day of November, 1993

Attest:

BRUCE LEHMAN

Attesting Officer

Commissioner of Patents and Trademarks